US006251623B1

(12) United States Patent
Arahira et al.

(10) Patent No.: US 6,251,623 B1
(45) Date of Patent: Jun. 26, 2001

(54) QUICK ASSAY METHOD FOR THE ACTIVITY OF A PLANT-DERIVED, ASPARAGINE RESIDUE-SPECIFIC ENDOPROTEASE

(75) Inventors: Masaomi Arahira; Chikafusa Fukazawa, both of Tsukuba (JP)

(73) Assignee: Director of National Food Research Institute, Ministry of Agriculture, Forestry and Fisheries, Tsukuba (JP)

( * ) Notice: Subject to any disclaimer, the term of this patent is extended or adjusted under 35 U.S.C. 154(b) by 0 days.

(21) Appl. No.: 09/410,025

(22) Filed: Oct. 1, 1999

(30) Foreign Application Priority Data

Nov. 4, 1998 (JP) .................................. 10-327536

(51) Int. Cl.[7] .............................. C12Q 1/37; C12Q 1/00; C12N 9/00
(52) U.S. Cl. .................................. 435/23; 435/24; 435/4; 435/183; 435/219; 435/814
(58) Field of Search .................................. 435/23, 24, 4, 435/183, 219, 814

(56) References Cited

U.S. PATENT DOCUMENTS

| | | | |
|---|---|---|---|
| 5,094,952 | * | 3/1992 | Matsushita et al. .................. 435/212 |
| 5,120,644 | * | 6/1992 | Ikenaka et al. ......................... 435/15 |
| 5,739,025 | * | 4/1998 | Fukazawa ............................. 435/219 |
| 6,107,471 | * | 8/2000 | Arahira et al. ....................... 536/23.2 |

* cited by examiner

Primary Examiner—Louise N. Leary
(74) Attorney, Agent, or Firm—Oblon, Spivak, McClelland, Maier & Neustadt, P.C.

(57) ABSTRACT

A quick assay method for the activity of a plant-derived, asparagine residue-specific endoprotease is disclosed which comprises measuring fluorescence generated by a fluorescence quenching substrate split by an asparagine residue-specific endoprotease. The fluorescence quenching substrate comprises an oligopeptide having in its amino acid sequence at least one asparagine residue, whose C-terminal side is other than an isoleucine residue, a leucine residue, or a valine residue, wherein the oligopeptide has a 7-methoxycoumarin-4-yl-acetyl group arranged on its N-terminal side and a 2,4-dinitrophenyl group arranged on its C-terminal side.

3 Claims, 5 Drawing Sheets

QUICK ASSAY METHOD FOR THE ACTIVITY OF A PLANT-DERIVED, ASPARAGINE RESIDUE-SPECIFIC ENDOPROTEASE

FIELD OF THE INVENTION

The present invention relates to a quick assay method for the activity of a plant-derived, asparagine residue-specific endoprotease and more particularly to a method for quickly assaying the activity of a plant-derived, asparagine residue-specific endoprotease utilizing a fluorescence quenching substrate having a specified structure.

BACKGROUND OF THE INVENTION

Asparagine residue-specific endoproteases refer to enzymes which split an amino acid sequence of peptide or protein at the C-terminal side of asparagine residue. Among them, the asparagine residue-specific endoprotease derived from plants is called legumaturain.

Legumaturain is an enzyme which is involved in synthesis of storage proteins of plant seeds that are useful as an excellent protein source in food industry, etc.

For example, soybean glycinin is synthesized as a soybean glycinin precursor consisting of a single polypeptide originally in the form of an acidic subunit and a basic subunit bonded to each other. The precursor must be subjected to a subsequent action of legumaturain to be split between the subunits before it can be converted into a mature form, glycinin.

Therefore, the enzyme activity of legumaturain influences the industrial feasibility of storage proteins such as glycinin.

Under the circumstances, there has been demanded an accurate assay method for assaying the enzyme activity of legumaturain and conventionally the following methods have been used (cf. Japanese Patent Publication No. Hei 8-24576).

(1) Qualitative Measurement Method by an Immunoblot Method

This is a method in which a natural 11S type seed storage protein precursor inclusive of a precursor such as soybean glycinin is expressed in an *Escherichia coli* cell and purified, the precursor is split with legumaturain to produce an acidic subunit and a basic subunit, which are separated by SDS-PAGE and blotted to PVDF membrane and subsequently the subunits were qualitatively detected by immunoblot method at high sensitivity using an antibody to the basic subunit.

(2) Assay Method of the Activity by Fractionating Split Synthetic Peptide by High Performance Liquid Chromatography This is a method in which legumaturain is acted on a synthetic peptide containing an asparagine residue, subsequently the substrate and resultant peptide were separated from each other using an inverse phase column connected to a high performance liquid chromatography apparatus, and its splitting activity is assayed.

However, the method (1) above takes totally about one day for the assay so that it cannot be said to be a quick assay method although it has advantages that it can assay relatively a large numbers of samples at a time and has a very high sensitivity. Also, the method (2) takes about 30 minutes per sample.

Furthermore, in the methods (1) and (2), contamination of protease other than legumaturain in samples makes it difficult to perform an accurate assay.

Therefore, the above-described conventional methods for assaying the activity of legumaturain have been defective in operability, quickness, etc.

SUMMARY OF THE INVENTION

An object of the present invention is to provide a method for assaying the enzymatic activity of legumaturain which can overcome the above-described problems of the prior art and quickly assay the enzymatic activity of legumaturain specifically and in a simple and easy manner.

Absorptiometry, fluorimetry and the like are generally employed as a quick assay method of enzymatic activity.

Generally known method for assaying the enzymatic activity of endoproteases specific to an asparagine residue includes a method which assays an amidase activity, which is an activity of releasing an amino group from an amidated amino acid, instead of assaying the protease activity.

That is, there have already been reported several methods in which there is provided a peptide whose asparagine residue at the C-terminal side has an amidated carboxyl group and an asparagine residue-specific endoprotease is acted on said peptide to assay its activity.

More specifically, there have been reported (3) a method in which a peptide is synthesized whose asparagine residue has a carboxyl group to which an amino group is bonded and the amidase 2 activity of the peptide is assayed by high performance liquid chromatography (Abe Y. et al., Journal of Biological Chemistry, 268, 3525–3529 (1993)), (4) a method in which a peptide is synthesized whose asparagine residue has a carboxyl group to which a 7-amino-4-methylcoumarin is bonded and its amidase activity is assayed by fluorimetry (Asha A. Kembhavi et al., Archives of Biochemistry and Biophysics, 303, 208–213 (1993)), etc.

As in the assay methods (3) and (4), it is a simple and easy method to assay amidase activity instead of protease activity as used for trypsin, papain, etc.

Accordingly, the present inventors conducted the assay of legumaturain, whose enzymatic activity had already been confirmed by the methods (1) and (2) as described, with regard to its amidase activity by the methods (3) and (4), respectively.

However, legumaturain exhibited no amidase activity by these methods.

That is, in the assay methods (3) and (4), what is assayed is the activity of amidase, which is a contaminant, that is, the activity of releasing an amino group from an amidated amino acid, is just assayed as the effect of asparaginase, but not the activity of legumaturain, which specifically acts on asparagine residues to split its C-terminal side.

Therefore, it has been revealed that upon assaying the activity of legumaturain, a method using a peptide whose asparagine residue has an amidated carboxyl group at the C-terminal side thereof cannot be adopted.

Accordingly, the present inventors have synthesized various types of peptides and examined the properties of legumaturain. More specifically, various peptides were synthesized based on the splitting site of acidic subunit and basic subunit of $A_2B_{1a}$ subunit from among the soybean glycinin precursor subunits and their splitting properties by legumaturain were examined.

As a result, it has now been elucidated that legumaturain shows no splitting activity to peptides whose asparagine residues exist on the N-terminal side and C-terminal side and it exhibits its activity according to a certain splitting rule. Furthermore, it has now been found that use of a fluorescence quenching substrate synthesized based on the splitting rule allows legumaturain activity to be assayed quickly and at high sensitivity. The present invention has been completed on the findings.

That is, in a first aspect, the present invention provides 1) a quick assay method for the activity of a plant-derived, asparagine residue-specific endoprotease, comprising measuring fluorescence generated by a fluorescence quenching substrate split by an asparagine residue-specific endoprotease, the fluorescence quenching substrate comprising an oligopeptide having in its amino acid sequence at least one asparagine residue, whose C-terminal side is other than an isoleucine residue, a leucine residue, or a valine residue, wherein the oligopeptide has a 7-methoxycoumarin-4-yl-acetyl group arranged on its N-terminal side and a 2,4-dinitrophenyl group arranged on its C-terminal side.

In a second aspect, the present invention provides 2) a quick assay method as described in 1) above, wherein the fluorescence quenching substrate is any one oligopeptides described in Sequence I. D. Nos. 1 to 6 of the sequence list, the oligopeptide having a 7-methoxycoumarin-4-yl-acetyl group arranged on its N-terminal side and a 2,4-dinitrophenyl group arranged on its C-terminal side.

In a third aspect, the present invention provides 3) a quick assay method as described in 1) or 2) above, wherein the fluorescence quenching substrate is any one oligopeptides described in Sequence I. D. Nos. 1 to 6 of the sequence list, the oligopeptide having a 7-methoxycoumarin-4-yl-acetyl group arranged on an amino group in a glycine residue at its N-terminal side and a 2,4-dinitrophenyl group arranged on an ε-amino group in a third lysine residue from its C-terminal side.

The method of the present invention enables one to quantitatively assay a plant-derived, asparagine residue-specific endoprotease, by merely measuring the intensity of fluorescence emitted by making an enzyme act on a specified fluorescence quenching substrate. Therefore, it is more simple and easier than the conventional methods and it can allow the assay in a short period of time.

Further, the method of the present invention enables one to conduct likewise quickly and in a short period of time specific quantitative assay of an enzyme even in samples which contain a large amount of other proteases or substance that inhibit fluorescence, for example, crude extracts.

Further, use of the quantitative assay method of the present invention enables one to assay the enzymatic activity at a very high sensitivity. For example, assay is possible at such a weak enzymatic activity that about 0.3 pmol of split peptide is obtained from 1.5 nmol of peptide per minute.

DETAILED DESCRIPTION OF THE INVENTION

Figure 1:
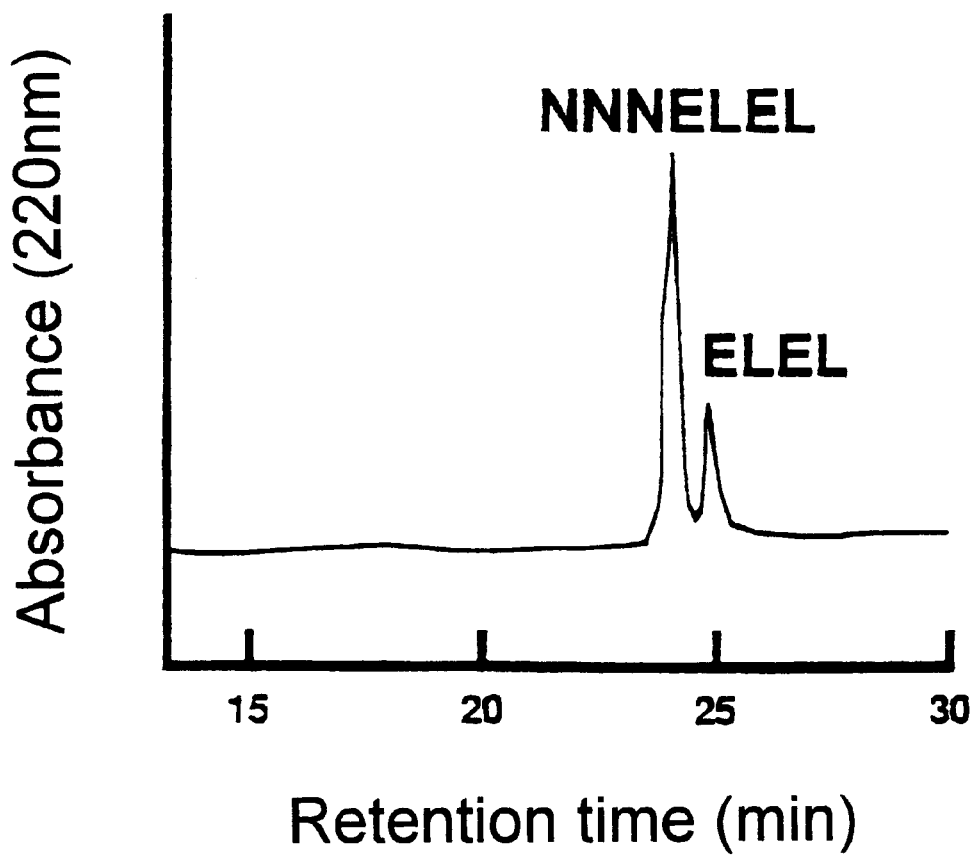
FIG. 1 is a HPLC pattern illustrating the decomposition rule of a synthetic peptide by legumaturain.

Hereafter, the present invention will be described in detail.

The enzyme used in the present invention is a plant-derived, asparagine residue-specific endopeptidase, i.e., legumaturain. Specific examples of this enzyme include the one which is involved in the maturation of glycinin by splitting a soybean glycinin precursor between its subunits. The physical and chemical properties of the enzyme are described in Japanese Patent Publication No. Hei 8-24576.

The feature of the method of the present invention is in the use of a fluorescence quenching substrate in assaying the enzymatic activity of the above-described asparagine-specific endopeptidase.

The fluorescence quenching substrate is an oligopeptide having in its amino acid sequence at least one asparagine residue, and the C-terminal side of the asparagine residue is other than an isoleucine residue, a leucine residue, or a valine residue. The oligopeptide has a 7-methoxycoumarin-4-yl-acetyl group arranged on its N-terminal side and a 2,4-dinitrophenyl group arranged on its C-terminal side.

The present inventors took note of the fact that legumaturain attacks and splits between the acidic subunit and basic subunit in $A_2B_{1a}$ subunit from among soybean glycinin precursor subunits and also the fact that an oligopeptide obtained based on an amino acid sequence at the split side is useful for assaying legumaturain.

It revealed that a fluorescence quenching substrate obtained by modifying a peptide designed based on the concerned portion with a fluorescent group and a quencher therefor is useful in the assay of the enzymatic activity of asparagine residue-specific endopeptidase.

Up to date, no report has been made of an example of use of such a fluorescence quenching peptide for assaying the enzymatic activity of legumaturain.

The amino acid sequence of oligopeptide in a fluorescence quenching substrate, must be one which is a target of the enzymatic action of legumaturain.

As described above, legumaturain is an enzyme which splits the peptide chain on the C-terminal side of asparagine residue. Therefore, the oligopeptide must contain at least one asparagine residue in its amino acid sequence. However, from the viewpoint of the enzymatic specificity of legumaturain, it is necessary that the asparagine residue is neither on the N-terminal nor C-terminal. Also, it is preferred that the asparagine residue is positioned at the third residue or subsequent thereto counted from the N-terminal since it is more susceptible to the action of legumaturain with that structure.

Also, it is necessary that the residue adjacent to the C-terminal side of asparagine residue is other than any of an isoleucine residue, a leucine residue, and a valine residue. This is because, such amino acid residues if present will adversely affect the enzymatic activity of legumaturain.

The oligopeptide portion as described above is preferably an amino acid sequence described in SEQ ID NOS: 1 to 6 of the sequence list attached hereto as described in the invention according to the second aspect above.

Furthermore, of these 6 sequences, it is more preferred that the residue adjacent to the second residue counted from the C-terminal side of the asparagine residue is an isoleucine residue, a leucine residue or a valine residue since with that structure, the enzymatic activity is remarkable and high fluorescence intensity is observed.

The number of residues of peptide is preferably 7 to 12 from the viewpoint of handling.

The fluorescence quenching peptide has a (7-methoxycoumarin-4-yl) acetyl group (hereafter, referred to as "MOCAc" group), a fluorescent group, on the N-terminal side of the above-described oligopeptide portion.

The MOCAc group is a strong fluorescent group which can generate a strong fluorescence when the oligopeptide of a fluorescence quenching substance is split by legumaturain.

The fluorescent group is arranged on an amino acid residue on the N-terminal side. The term "N-terminal side" means that the residue concerned is positioned closer to the N-terminal than the asparagine residue that is split by legumaturain. It is preferred that the fluorescent group is bonded to an amino group in the amino acid at the N-terminal as is disclosed in the third aspect of the present invention.

Although the kind of amino acid residue on the N-terminal side is not limited particularly but it is preferably the one derived from glycine, tyrosine or aspartic acid.

On the other hand, on the amino acid at the C-terminal of the oligopeptide portion of a fluorescence quenching substrate is arranged a 2,4-dinitrophenyl group (hereafter, referred to as "Dnp" group), an effective quencher (fluorescence absorbing group) for a MOCAc group.

The fluorescence quenching substrate with a Dnp group arranged on the C-terminal side will not generate fluorescence by a MOCAc group before it is split by legumaturain. When subjected to the action of the enzyme, the substrate is split into an N-terminal side having a MOCAc group and a C-terminal side having a Dnp group. Then, the fragment of N-terminal side having a MOCAc group will no longer be susceptible to the influence of the Dnp group so that fluorescence is generated.

Here, the term "C-terminal side" means usually an amino acid residue up to the second residue counted from the C-terminal. The amino acid on which a Dnp group is arranged is not limited particularly. However, it is preferred that the amino acid is a lysine residue and a Dnp group is bonded to its $\epsilon$-amino group as is disclosed in the third aspect of the present invention.

Such a fluorescence quenching peptide as having a MOCAc group on the N-terminal side and a Dnp group on the C-terminal side, that is, MOCAc-Dnp type peptide, has a feature that it has an excitation wavelength (Ex) of 328 nm and a fluorescence wavelength (Em) of 393 nm, which are sufficiently remote from each other, so that it shows a low background for fluorescence.

The assay method of the present invention is a method in which the above-described fluorescence quenching substrate is subjected to an enzymatic reaction with legumaturain, i.e., the target of measurement, and the fluorescence generated is measured by the intensity of fluorescence.

Usually, the enzymatic reaction is conducted using a reaction mixture containing a substrate and an enzyme specimen dissolved in a solvent. For example, the reaction is carried out as follows.

The reaction mixture can be constituted by a buffer solution such as a citric acid buffer solution of pH 6 to 7, a specimen containing legumaturain, a fluorescence quenching substrate, a reducing agent such as dithiothreitol, a surfactant such as Briji type surfactant, and other component (s).

Since the fluorescence quenching substrate has a high hydrophobicity, it has a poor solubility in the reaction mixture. Therefore, usually it is first dissolved in dimethyl sulfoxide (DMSO) before it can be added to the reaction mixture.

Here, DMSO is used in such an amount that its concentration in the reaction mixture is usually 4% (v/v) or less. If the amount of DMSO exceeds this range, it is possible that DMSO will inhibit the activity of legumaturain.

The amount of fluorescence quenching substrate to be added to the reaction mixture is preferably 5 to 40 $\mu$l per ml of the reaction mixture when the substrate is dissolved in DMSO in a concentration of 0.2 mM. Above this range, fluorescence will be excessive. On the other hand, below this range, no fluorescence will be observed so that the assay of the enzymatic activity will be hindered.

The reaction is carried out by allowing the above-described reaction mixture to stand usually at 20 to 37° C., preferably 35° C., for 5 to 60 minutes, preferably for 15 minutes. During the enzymatic reaction, the fluorescence quenching substrate is decomposed by the legumaturain contained in the specimen to generate fluorescence. For example, when the fluorescence quenching substrate used is a MOCAc-Dnp type peptide in which MOCAc and Dnp are arranged on the amino group in a glycine residue at the N-terminal and on the $\epsilon$-amino group in a lysine residue at the C-terminal, respectively, of the amino acid sequence described in Sequence I. D. No. 1., splitting occurs between asparagine (the sixth from the N-terminal and glycine (the seventh from the N-terminal) of the fluorescence quenching substrate by the enzymatic reaction.

After the enzymatic reaction is stopped by addition of a reaction terminator such as acetic acid, the intensity of fluorescence of the fluorescence quenching substrate generated by the enzymatic reaction is measured. As for the measuring apparatus, there can be used usually used one. For example, measurement can be conducted using Fluorimeter F2000, manufactured by Hitachi, Ltd.

Comparing the measured fluorescence intensity with the measured value of other specimen gives a relative enzyme activity.

Also, collation of the measured fluorescence intensity with the enzymatic activity of the same specimen already assayed by other means such as high performance liquid chromatography, the corresponding enzyme can be assayed quantitatively.

Therefore, in the method of the present invention, measurement can be performed not only with specimens containing only legumaturain but also with samples containing a large amount of other protease or a substance which inhibits fluorescence, for example, crude extracts.

That is, as a result of fluorimetry of samples by the method of the present invention, an estimation of activity can be made, even if there is the possibility that a sample contains a substance which inhibits fluorescence, by assaying the enzymatic activity of an index peptide such as a peptide having a sequence of NNNELEL (Asp Asp Asp Glu Leu Glu Leu) used in Example 1 hereinbelow instead of a fluorescence quenching substrate by high performance liquid chromatography (HPLC) and collating the assayed value with the earlier measured fluorescence intensity values.

EXAMPLES

Hereafter, the present invention will be described in more detail by examples. However, the present invention should no be construed as being limited thereto.

Example 1

[Detection of the activity of asparagine residue-specific endoprotease of legumaturain]

(1) Measurement of fluorescence intensity of MOCAc-Dnp type fluorescence quenching substrate A MOCAc-Dnp type peptide was prepared by arranging a MOCAc group on an amino group in the glycine residue at the N-terminal and a Dnp group on an 6-amino group in the third lysine residue counted from the C-terminal, respectively, of the oligopeptide (cf. SEQ ID NO: 1 of the sequence list) which was designed based on the splitting site of acidic subunit and basic subunit in the $A_2B_{1a}$ subunit from among the soybean glycinin precursor subunits. This was used as a fluorescence quenching substrate (hereafter, referred to as "substrate 1").

The substrate 1 was dissolved in DMSO to a concentration of 0.2 mM and the solution was used for preparing a reaction mixture having the composition shown in Table 1.

TABLE 1

[Composition of Reaction Mixture]

| | |
|---|---|
| 100 mM Citric acid Buffer solution (pH 6.8) | 100 µl |
| 0.1 M Dithiothreitol (DDT) | 10 µl |
| 0.2 mM fluorescence quenching substrate | 20 µl |
| 3% Briji 35 | 3 µl |
| Deionized H₂O | 857 µl |
| Enzyme solution | 10 µl |
| Total | 1 ml |

The above-described reaction mixture was subjected to enzymatic reaction at 35° C. for 15 minutes and stopped by addition of 100 µl of 5N acetic acid.

The fluorescence of the reaction mixture was measured by a fluorimeter F2000 manufactured by Hitachi, Ltd. As a result, fluorescence at a fluorescence wavelength (Em) of 393 n was observed at an excitation wavelength (Ex) of 328 nm.

From this it revealed that legumaturain contained in the reaction mixture initiated enzymatic reaction to split the peptide chain between the asparagine residue and glycine residue of the fluorescence quenching substrate (substrate 1).

(2) Relationship between the fluorescence intensity of MOCAc-Dnp type fluorescence quenching substrate and the amount of split peptide Next, in (1) above, actualenzymaticactivity (amount of split peptide) when the fluorescence intensity was 100 was measured by high performance liquid chromatography and relationship between the measured fluorescence intensity and the amount of split peptide was examined.

A reaction mixture having the same composition as shown in Table 1 was used except that instead of the substrate 1, there was used a synthetic peptide having a sequence of NNNELEL (Asp Asp Asp Glu Leu Glu Leu) (SEQ ID NO: 11) (hereafter, referred to as "NNNELEL peptide") in a concentration of 1.5 nmol. The enzymatic reaction conditions were 35° C. for 15 minutes so as to coincide with the conditions under which fluorescence intensity of 100 was obtained in the earlier fluorescence tests.

Note that when the NNNELEL peptide is subjected to the action of legumaturain, it will be split into NNN and ELEL fragments.

Using high performance chromatography apparatus (LC-6AD, manufactured by Shimadzu) connected with an inverse column (Silica ODS 120T, φ4.6 mm×150 mm, manufactured by Tosoh), a suitable amount of the reaction mixture was fractionated at a flow rate of 1 ml/minute for 30 minutes under a linear concentration gradient of 0.1% TFA to 0.1% TFA/30% acetonitrile according to the manual of the column. The detection of a peak was performed at a wavelength of 220 nm using SPD-6AV manufactured by Shimadzu.

As a result, a HPLC pattern was obtained which illustrates the decomposition rule of the synthetic peptide by legumaturain (FIG. 1). Table 2 shows the results of assay of the splitting activity of legumaturain on NNNELEL peptide.

TABLE 2

[Splitting activity of legumaturain on NNNELEL peptide by HPLC]

| | Substrate before reaction (1.5 nmol) | Substrate after reaction | Product after reaction | Splitting ratio (%) |
|---|---|---|---|---|
| Area | 12,000 | 8,000 | 4,000 | 33.3 |

FIG. 1 and Table 2 indicate that the fluorescence intensity obtained in (1) above at a fluorescence intensity of 100 corresponds to the case where 0.5 nmol of ELEL peptide was released from 1.5 nmol of NNNELEL peptide by legumaturain.

From the above-described results of measurement, it is apparent that the fluorescence intensity at the time when one third of 1.5 nmol peptide was split in 15 minutes from the initiation of the enzymatic reaction is 100, so that when the fluorescence intensity is one hundredth in 15 minutes, i.e., 1, the amount of peptide to be released is 0.005 nmol. This means that the amount of split peptide per minute is only 0.3 pmol.

According to the method of the present invention, detection is possible even when the fluorescence intensity is 1 or more, i.e., when only 0.3 pmol of peptide is split. Therefore, the method is shown to be a method which is simple and easy and has high sensitivity.

Comparative Example 1

[Assay of legumaturain activity using the synthetic peptide of Abe Y. et al.

Using the synthetic peptide obtained by the method described in Abe Y. et al., Journal of Biological Chemistry, 268, 3525–3529 (1993), the assay of legumaturain activity was tried.

First, a substrate A was prepared by arranging a Dnp group on an amino group of the proline residue at the N-terminal of a peptide consisting of Pro-Glu-Ala-Asn, and amidating the carboxyl group of the asparagine residue at the C-terminal of the peptide.

For the legumaturain which was confirmed to have a fluorescence intensity of 40 when assayed with the substrate 1 at 35° C. for 15 minutes, the activity was assayed using the substrate A instead of the substrate 1.

That is, a 50 µl (substrate: 20 µM) reaction mixture having the same composition as shown in Table 1 used in Example 1 was prepared, which was subjected to enzymatic reaction for a predetermined time shown in Table 3 (0, 15, 30, 60, or 120 minutes). To each reaction mixture was added 5 µl of formic acid to stop the reaction.

After the reaction was stopped, the reaction mixture was applied to HPLC and the enzymatic activity was assayed under the same conditions as in Example 1. Detection was carried out at 350 nm using an elution solvent of 47 mM acetic acid buffer solution (pH 4.5)/20% acetonitrile. Table 3 shows the results of incubation at 35° C. up to 120 minutes from the initiation of the reaction.

TABLE 3

[Splitting activity of the peptide of Abe Y. et al.]

| | Reaction Time (Minute) | | | | |
|---|---|---|---|---|---|
| | 0 | 15 | 30 | 60 | 120 |
| Area (substrate) | 10,000 | 10,000 | 10,000 | 10,000 | 10,000 |

Table 3 indicates that legumaturain does not decompose the above-described substrate.

From this, it is apparent that the enzymatic activity of legumaturain cannot be assayed by use of the peptide described in Abe Y. et al. (supra).

Comparative Example 2

[Assay of enzymatic activity of legumaturain by use of the synthetic peptide of Asha A. Kembhavi et al.]

Using the synthetic peptide obtained by the method described in Asha A. Kembhavi et al., Archives of Biochemistry and Biophysics, 303, 208–213 (1993), the assay of legumaturain activity was tried.

A substrate B was prepared by arranging a benzyloxycarbonyl group on the amino group in the phenylalanine residue at the N-terminal of a peptide consisting of Phe-Ala-Ala-Asn whereas 7-(4-methyl) coumarylamidating the carboxyl group in the asparagine residue at the C-terminal side of the peptide.

For the legumaturain which was confirmed to have a fluorescence intensity of 40 when assayed with the substrate 1 at 35° C. for 15 minutes, the activity was assayed using the substrate B instead of the substrate 1.

That is, a 1 mM (substrate: 10 μM) reaction mixture having the same composition as shown in Table 1 used in Example 1 was prepared and subjected to enzymatic reaction in the same manner as in Comparative Example 1.

Fluorimetric measurement of the reaction mixture was performed at λEx=360 nm and λEm=460 nm. Table 4 shows the results.

TABLE 4

[Splitting activity of the peptide of Asha A. Kembhavi et al.]

| | Time from the initiation of the enzyme reaction | | | | |
|---|---|---|---|---|---|
| | After 0 min. | After 15 min. | After 30 min. | After 60 min. | After 120 min. |
| Fluorescence intensity | 0 | 0 | 0 | 0 | 0 |

As will be apparent from Table 4, no fluorescence was observed from the reaction mixture of the substrate B.

This indicates that legumaturain has no ability of decomposing the above-described substrate B, so that the enzymatic activity of legumaturain cannot be assayed by use of the peptide described in Asha A. Kembhavi et al. (supra).

Example 2

[Examination of the amino acid sequence of fluorescence quenching substrates]

By substituting an other residue for a portion of the amino acids in the substrate 1 prepared based on the sequence of soybean glycinin precursor subunit used in Example 1, 9 kinds of fluorescence quenching substrates (hereafter, referred to substrates 2 to 10, respectively) were synthesized. The peptide portions of substrates 2 to 10 have respective sequences shown in Sequence I. D. Nos. 2 to 10 of the sequence list.

The sequences of the substrates 2 to 10 resulted by substitution of a portion of the sequence of the substrate 1, etc. That is, the substrates 2 to 4 (cf. SEQ ID NOS: 2 to 4 of the sequence list) correspond to the sequences obtained by substituting the isoleucine residue which is the eighth counted from the N-terminal (by 2 residues on the C-terminal side from the N) in the substrate 1 (cf. SEQ ID NO: 1 of the sequence list) with a leucine residue, avaline residue, oraglycineresidue, respectively.

The substrates 5 and 6 (cf. SEQ ID NOS: 5 and 6 of the sequence list) correspond to the sequences obtained by substituting the glycine residue which is the seventh counted from the N-terminal (by 1 residue on the C-terminal side from the N) in the substrate 1 with an arginine residue or an alanine residue, respectively.

The substrates 7 to 9 (cf. SEQ ID NOS: 7 to 9 of the sequence list) correspond to the sequences which were obtained by mutually replacing the seventh and eighth amino acids counted from the N-terminal in the substrates 1 to 3, respectively.

The substrate 10 (cf. SEQ ID NO: 10 of the sequence list) corresponds to the sequence obtained by substituting the asparagine residue which is the sixth counted from the N-terminal of the substrate 1 with an aspartic acid residue.

The enzymatic activity of each substrate was assayed in the same manner as in Example 1. Table 5 shows the results.

TABLE 5

[Legumaturain activity on 10 kinds of synthesized fluorescence quenching substrate]

| Substrate | Sequence | Background | Fluorescence intensity | Activity (pmol/min.) |
|---|---|---|---|---|
| 1 | Sequence I.D. No. 1 | 15.3 | 323 | 103 |
| 2 | Sequence I.D. No. 2 | 15.3 | 354 | 113 |
| 3 | Sequence I.D. No. 3 | 15.6 | 318 | 11 |
| 4 | Sequence I.D. No. 4 | 15.4 | 238 | 74 |
| 5 | Sequence I.D. No. 5 | 15.5 | 206 | 64 |
| 6 | Sequence I.D. No. 6 | 15.5 | 206 | 64 |
| 7 | Sequence I.D. No. 7 | 15.1 | 15.2 | 0 |
| 8 | Sequence I.D. No. 8 | 15.5 | 15.1 | 0 |
| 9 | Sequence I.D. No. 9 | 15.9 | 15.4 | 0 |
| 10 | Sequence I.D. No.10 | 15.7 | 15.3 | 0 |

Table 5 indicates the following points.

First, since no emission of fluorescence by the substrate 10 is observed, peptides without containing asparagine residue are not split and no enzymatic reaction occurs. This indicates that from the viewpoint of the specificity of legumaturain to an asparagine residue, fluorescence quenching substrates that show an enzymatic activity must always contain an asparagine residue.

Next, of the substrates 1 to 9 having each an asparagine residue, the substrates 2 to 6 show a high fluorescence intensity while the substrates 7 to 9 hardly emit fluorescence.

Among the substrates 2 to 6, which showed an enzymatic activity, the substrates 2 and 3 exhibit an activity equivalent to or higher than that of the substrate 1. This indicates that substitution of the isoleucine residue which is the second counted from the C-terminal of the asparagine residue in the substrate 1 with a leucine residue or a valine residue gives an enzymatic activity equal to or higher than that of the unsubstituted one.

Also, the substrates 4 to 6 also exhibited an enzymatic activity though not so high as those of the substrates 2 and 3. From the fluorescence intensity of the substrate 4, it can be seen that a fluorescence quenching substrate of which the second residue on the C-terminal side of the asparagine residue replaced by a glycine residue also is susceptible to the attack by legumaturain.

Furthermore, the results on the substrates 5 and 6 indicate that substitution of the first residue on the C-terminal side of the asparagine residue with an arginine residue or an alanine residue also retains the enzymatic activity.

On the other hand, in the case of the substrates 7 to 9, no enzymatic activity was observed. These substrates have a glycine residue as the second residue counted from the N-terminal. However, the substrate 4, which is similar thereto, showed good results. Considering this point, the reason why the substrates 7 to 9 exhibited no enzymatic activity is that the first residue counted from the C-terminal of the asparagine residue has been substituted with a leucine residue, an isoleucine residue, or a valine residue.

The above-described results proved that in the case of the substrate 1, which is a fluorescence quenching substrate designed based on a plant seed storage protein, an equivalent enzymatic activity can be observed even when its amino acid sequence is substituted under certain conditions.

Example 3
[Analysis of properties of legumaturain utilizing a fluorescence quenching substrate]

Tests were repeated in the same procedure as in Example 1 in which the substrate 1 was used except that the enzymatic reaction conditions were varied slightly in order to examine the pH stability, optimum pH, temperature stability and optimum temperature of legumaturain.

(1) Examination of optimum pH

Figure 2:
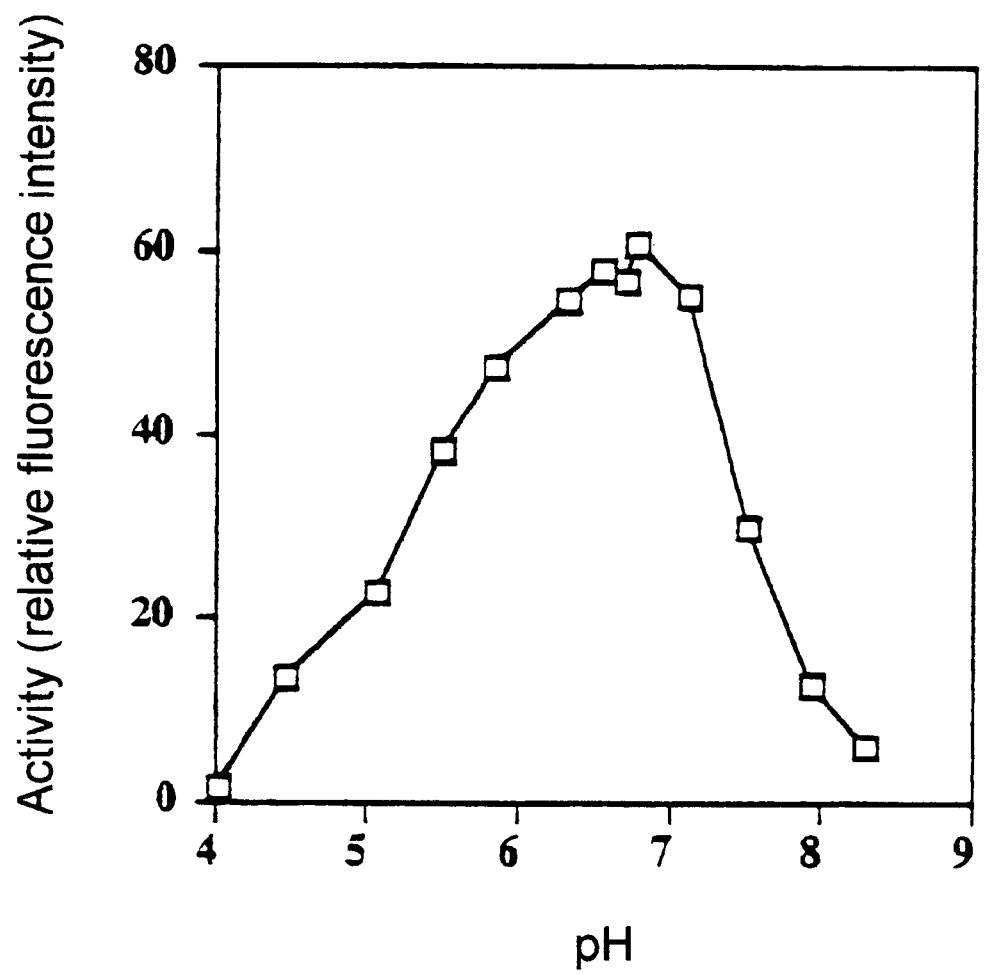
FIG. 2 is a graph illustrating the optimum pH of legumaturain, assayed with a use of fluorescence quenching substrate.

Using various buffer solutions, the pH at the time of enzymatic reaction was adjusted to pH 1.9 to 11.4 and the enzymatic activity was assayed. FIG. 2 illustrates the results of assay at pH 4 to 9.

FIG. 2 indicates that the highest fluorescence intensity is observed at pH 6.8 so that optimum pH of legumaturain is pH 6.8.

(2) Examination of pH stability

Figure 3:
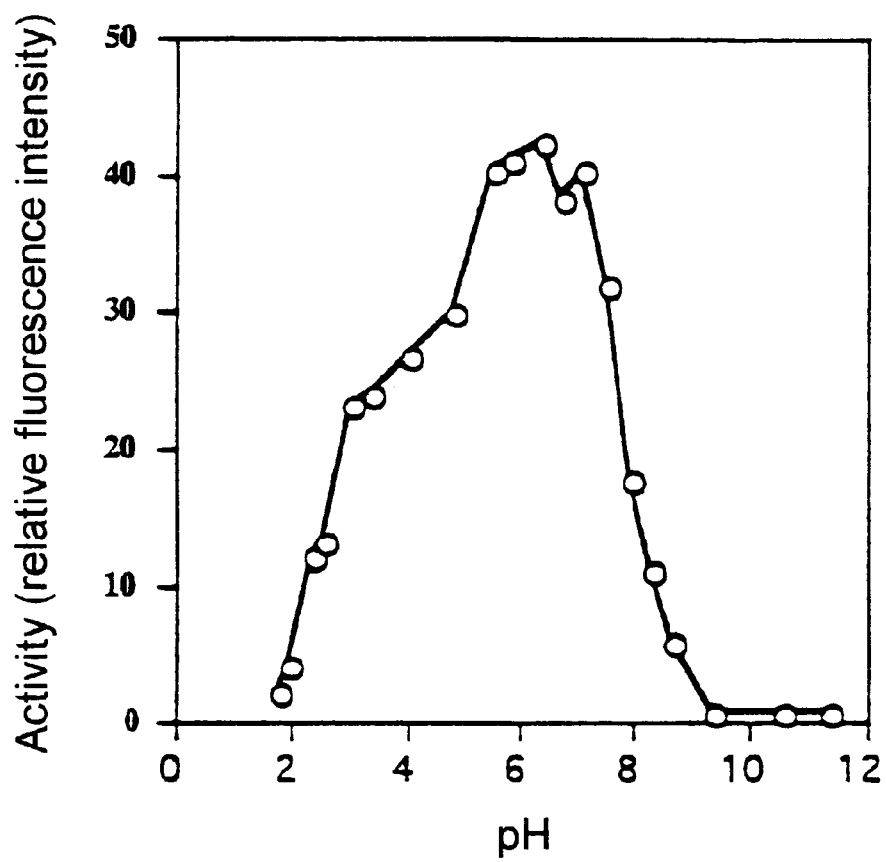
FIG. 3 is a graph illustrating the pH stability of legumaturain, assayed with a use of fluorescence quenching substrate.

In the same manner as in (1) above, the reaction mixture was adjusted to pH 1.9 to 11.4. After stored at 20° C. for 30 minutes, the pH was brought back to pH 6.8 with a use of buffer solution and then the enzymatic activity was assayed. FIG. 3 illustrates the results.

FIG. 3 indicates that the enzyme is stable between pH 2 to 9.

(3) Examination of optimum temperature

Figure 4:
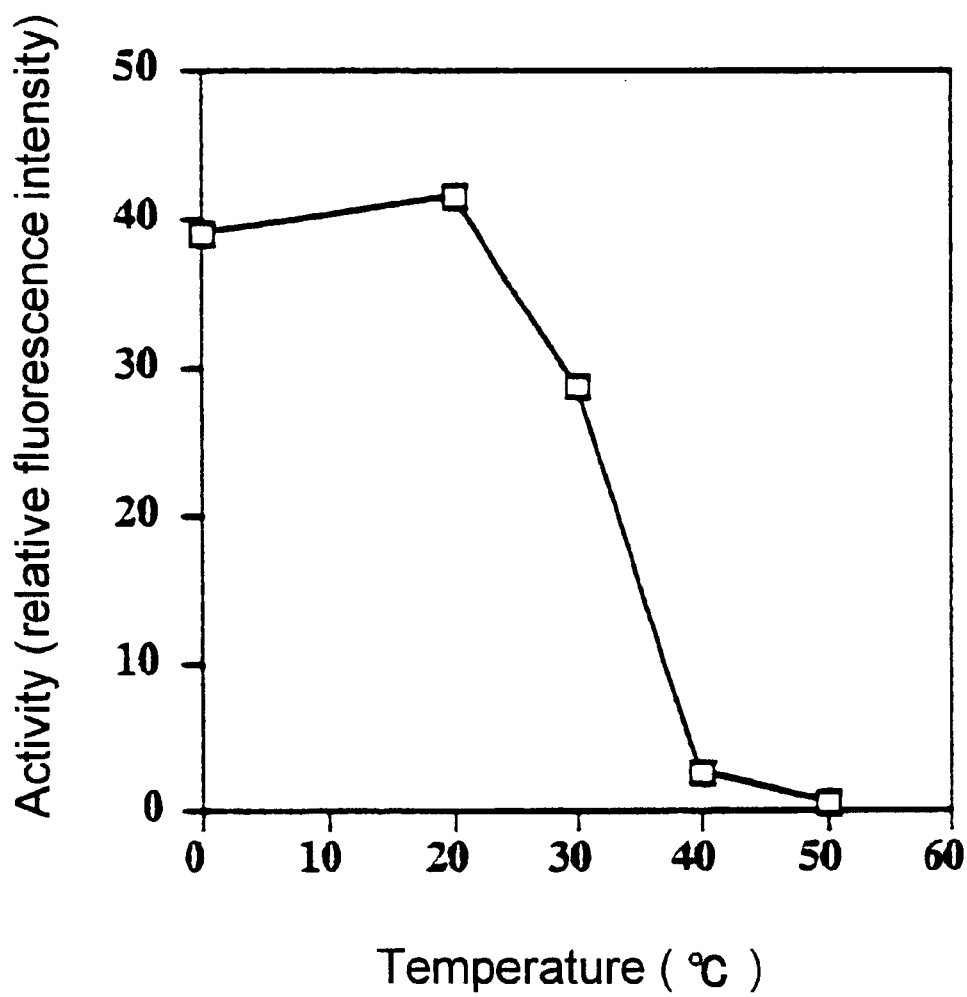
FIG. 4 is a graph illustrating the optimum temperature of legumaturain, assayed with a use of fluorescence quenching substrate.

Examination of optimum temperature was conducted in the same manner as in Example 1 except that the temperature of enzymatic reaction was varied between 0 to 60° C. FIG. 4 illustrates the results.

FIG. 4 indicates that the optimum temperature of the enzyme is 35° C.

(4) Examination of temperature stability

Figure 5:
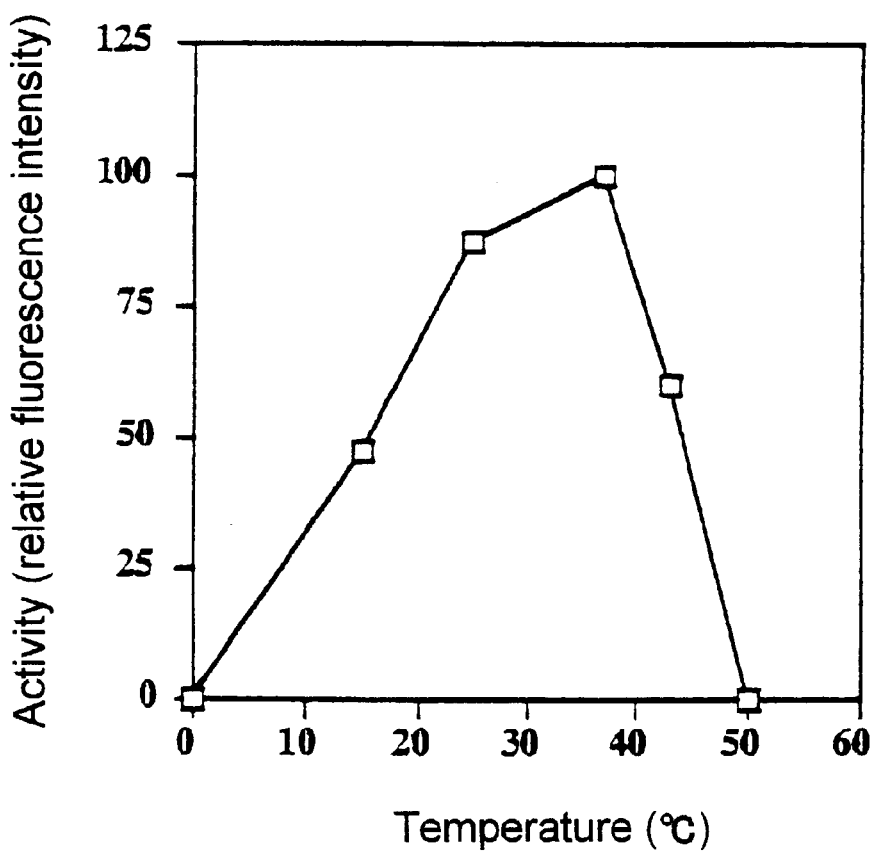
FIG. 5 is a graph illustrating the temperature stability of legumaturain, assayed with a use of fluorescence quenching substrate.

After the reaction mixture was left to stand at a temperature in the range of 0 to 60° C. for 30 minutes, it was brought back to the optimum condition (35° C.) before assaying the enzymatic activity. FIG. 5 illustrates the results.

FIG. 5 indicates that the enzyme has a very low stable temperature range as low as 0 to 20° C.

What is claimed is:

1. A quick assay method for evaluating the activity of a plant-derived, asparagine residue-specific endoprotease, comprising measuring fluorescence generated by a fluorescence quenching substrate split by an asparagine residue-specific endoprotease, and the fluorescence quenching substrate comprising an oligopeptide having an amino acid sequence with at least one asparagine residue, the C-terminal side is other than an isoleucine residue, a leucine residue, or a valine residue, wherein the oligopeptide has a 7-methoxycoumarin-4-yl-acetyl group arranged on the N-terminal side and a 2,4-dinitrophenyl group arranged on the C-terminal side.

2. The quick assay method as claimed in claim 1, wherein the fluorescence quenching substrate is any one of the oligopeptides described in Sequence I. D. Nos. 1 to 6 of the sequence list, the oligopeptide having a 7-methoxycoumarin-4-yl-acetyl group arranged on the N-terminal side and a 2,4-dinitrophenyl group arranged on the C-terminal side.

3. The quick assay method as claimed in claim 1 or 2, wherein the fluorescence quenching substrate is a oligopeptide selected from the group consisting of SEQ ID NOS: 1 to 6, the oligopeptide having a 7-methoxycoumarin-4-yl-acetyl group arranged on an amino group in a glycine residue at the N-terminal side and a 2,4-dinitrophenyl group arranged on an εamino group in a third lysine residue counted from the C-terminal side.

* * * * *

UNITED STATES PATENT AND TRADEMARK OFFICE
CERTIFICATE OF CORRECTION

PATENT NO.    : 6,251,623 B1
DATED         : June 26, 2001
INVENTOR(S)   : Masaomi Arahira et al.

Page 1 of 1

It is certified that error appears in the above-identified patent and that said Letters Patent is hereby corrected as shown below:

<u>Column 15,</u>
Line 14, "(Asn Asn Asn Glu Leu Glu Leu)" should read -- (Asp Asp Asp Glu Leu Glu Leu) --.

Signed and Sealed this

Twenty-third Day of April, 2002

Attest:

*Attesting Officer*

JAMES E. ROGAN
*Director of the United States Patent and Trademark Office*

SEQUENCE LISTING

```
<160> NUMBER OF SEQ ID NOS:  11

<210> SEQ ID NO 1
<211> LENGTH: 11
<212> TYPE: PRT
<213> ORGANISM: Glycine max

<400> SEQUENCE: 1

Gly Lys Ser Arg Arg Asn Gly Ile Lys Arg Arg
1               5                   10

<210> SEQ ID NO 2
<211> LENGTH: 11
<212> TYPE: PRT
<213> ORGANISM: Glycine max

<400> SEQUENCE: 2

Gly Lys Ser Arg Arg Asn Gly Leu Lys Arg Arg
1               5                   10

<210> SEQ ID NO 3
<211> LENGTH: 11
<212> TYPE: PRT
<213> ORGANISM: Glycine max

<400> SEQUENCE: 3

Gly Lys Ser Arg Arg Asn Gly Val Lys Arg Arg
1               5                   10
```

```
<210> SEQ ID NO 4
<211> LENGTH: 11
<212> TYPE: PRT
<213> ORGANISM: Glycine max

<400> SEQUENCE: 4

Gly Lys Ser Arg Arg Asn Gly Gly Lys Arg Arg
1               5                   10

<210> SEQ ID NO 5
<211> LENGTH: 11
<212> TYPE: PRT
<213> ORGANISM: Glycine max

<400> SEQUENCE: 5

Gly Lys Ser Arg Arg Asn Arg Ile Lys Arg Arg
1               5                   10

<210> SEQ ID NO 6
<211> LENGTH: 11
<212> TYPE: PRT
<213> ORGANISM: Glycine max

<400> SEQUENCE: 6

Gly Lys Ser Arg Arg Asn Ala Ile Lys Arg Arg
1               5                   10

<210> SEQ ID NO 7
<211> LENGTH: 11
<212> TYPE: PRT
<213> ORGANISM: Glycine max

<400> SEQUENCE: 7

Gly Lys Ser Arg Arg Asn Ile Gly Lys Arg Arg
1               5                   10

<210> SEQ ID NO 8
<211> LENGTH: 11
<212> TYPE: PRT
<213> ORGANISM: Glycine max

<400> SEQUENCE: 8

Gly Lys Ser Arg Arg Asn Leu Gly Lys Arg Arg
1               5                   10

<210> SEQ ID NO 9
<211> LENGTH: 11
<212> TYPE: PRT
<213> ORGANISM: Glycine max

<400> SEQUENCE: 9

Gly Lys Ser Arg Arg Asn Val Gly Lys Arg Arg
1               5                   10

<210> SEQ ID NO 10
<211> LENGTH: 11
<212> TYPE: PRT
<213> ORGANISM: Glycine max

<400> SEQUENCE: 10

Gly Lys Ser Arg Arg Asp Gly Ile Lys Arg Arg
1               5                   10
```

```
<210> SEQ ID NO 11
<211> LENGTH: 7
<212> TYPE: PRT
<213> ORGANISM: Artificial/Unknown
<220> FEATURE:
<221> NAME/KEY: misc_feature
<222> LOCATION: ()..()
<223> OTHER INFORMATION: Description of Artificial Sequence: synthetic
      peptide

<400> SEQUENCE: 11

Asn Asn Asn Glu Leu Glu Leu
1               5
```